US006448570B1

(12) United States Patent
Scherzer et al.

(10) Patent No.: US 6,448,570 B1
(45) Date of Patent: Sep. 10, 2002

(54) RADIANT DEVICE, ESPECIALLY INFRARED RADIATOR

(75) Inventors: Joachim Scherzer, Bruchkobel; Siegfried Grob, Hanau, both of (DE)

(73) Assignee: Heraeus Noblelight GmbH, Hanau (DE)

( * ) Notice: Subject to any disclaimer, the term of this patent is extended or adjusted under 35 U.S.C. 154(b) by 0 days.

(21) Appl. No.: 09/550,330

(22) Filed: Apr. 14, 2000

(30) Foreign Application Priority Data

Apr. 16, 1999 (DE) ........................................ 199 17 270

(51) Int. Cl.[7] ................................................ A61N 5/06
(52) U.S. Cl. .................................. 250/495.1; 250/493.1
(58) Field of Search ........................... 250/495.1, 493.1, 250/494.1; 219/553; 313/331

(56) References Cited

U.S. PATENT DOCUMENTS

| | | | | |
|---|---|---|---|---|
| 923,797 A | | 6/1909 | McNeill | |
| 4,959,587 A | * | 9/1990 | Schug | 313/623 |
| 5,123,868 A | | 6/1992 | Waymouth | |
| 5,567,951 A | | 10/1996 | Baschant et al. | |
| 6,057,532 A | * | 5/2000 | Dexter et al. | 219/553 |

FOREIGN PATENT DOCUMENTS

| | | |
|---|---|---|
| DE | 44 38 870 | 5/1996 |
| EP | 0 989 590 | 3/2000 |
| GB | 2 233 150 | 1/1991 |

* cited by examiner

*Primary Examiner*—Kiet T. Nguyen
(74) *Attorney, Agent, or Firm*—Oblon, Spivak, McClelland, Maier & Neustadt, P.C.

(57) ABSTRACT

A radiant device comprising an envelope tube, which tube contains a long axis, and inside the tube, at least one radiant source oriented in the direction of the long axis of the envelope tube which is sealed at both ends, with a metal, electrical connecting part at each end of the envelope tube, and at least one elastic intermediate part which absorbs length changes of the radiant source and which is firmly joined at one end to an electrical connecting part and at the other end to the radiant source, and wherein the intermediate part comprises a molybdenum sheet provided with at least one folding portion having two kink points perpendicular to the long axis.

20 Claims, 1 Drawing Sheet

RADIANT DEVICE, ESPECIALLY INFRARED RADIATOR

BACKGROUND OF THE INVENTION

1. Field of the Invention

The present invention relates to a radiant device, and preferably an infrared radiator, with at least one radiant source oriented in the direction of the long axis of an envelope tube which is sealed at both ends, with a metal, electrical connecting part at each end of the envelope tube and, inside the envelope tube, with at least one elastic intermediate part which absorbs the length changes of the radiant source and which is firmly joined at one end to an electrical connecting part and at the other end to the radiant source.

2. Description of the Background

Such radiant devices or radiators are generally known and are described, for example in British Patent Application GB A 2233150. The infrared radiant source presented in that application is provided with an envelope tube of material transparent to infrared radiation, which tube contains an electrical conductor formed from carbon fibers connected to an electrical power supply. The envelope tube is sealed at its ends and either can be evacuated or can be filled with a gas such as argon. There are thereby obtained radiant sources with rapid response behavior, which can be operated at temperatures above 1200° C. In the transition region between the electrical conductor and the connecting pins led out from the envelope tube at the ends thereof there is inserted, inside the envelope tube, a helically wound metal wire conductor, in order to compensate for the different length expansions, especially of the conductor, inside the envelope tube.

German Patent Application DE A 14419285 (equivalent to U.S. Pat. No. 5,567,951) also describes a radiant device, particularly an infrared radiator, with at least one flat-form radiant source. The radiant source is a carbon ribbon, which is disposed as a plurality of contiguous partial sections, the partial sections being held at their ends in supports, at least the first and last of which are formed as contacts. This radiant device is resistant to temperature fluctuations even over a prolonged time, and it also exhibits low inertia.

SUMMARY OF THE INVENTION

Starting from the prior art described above, the object of the present invention is to design a radiant device of the type described above in such a way that it can be constructed in particular with small fluorescent-tube or envelope-tube diameters, for example, with inside diameters in a range smaller than 12 mm, while at the same time ensuring that length changes in the radiant source can be compensated for.

This object is achieved in a radiant device of the type described above, wherein the intermediate part comprises a molybdenum sheet provided with at least one folding portion having two kink points perpendicular to the long axis.

DETAILED DESCRIPTION OF THE INVENTION

Figure 1:
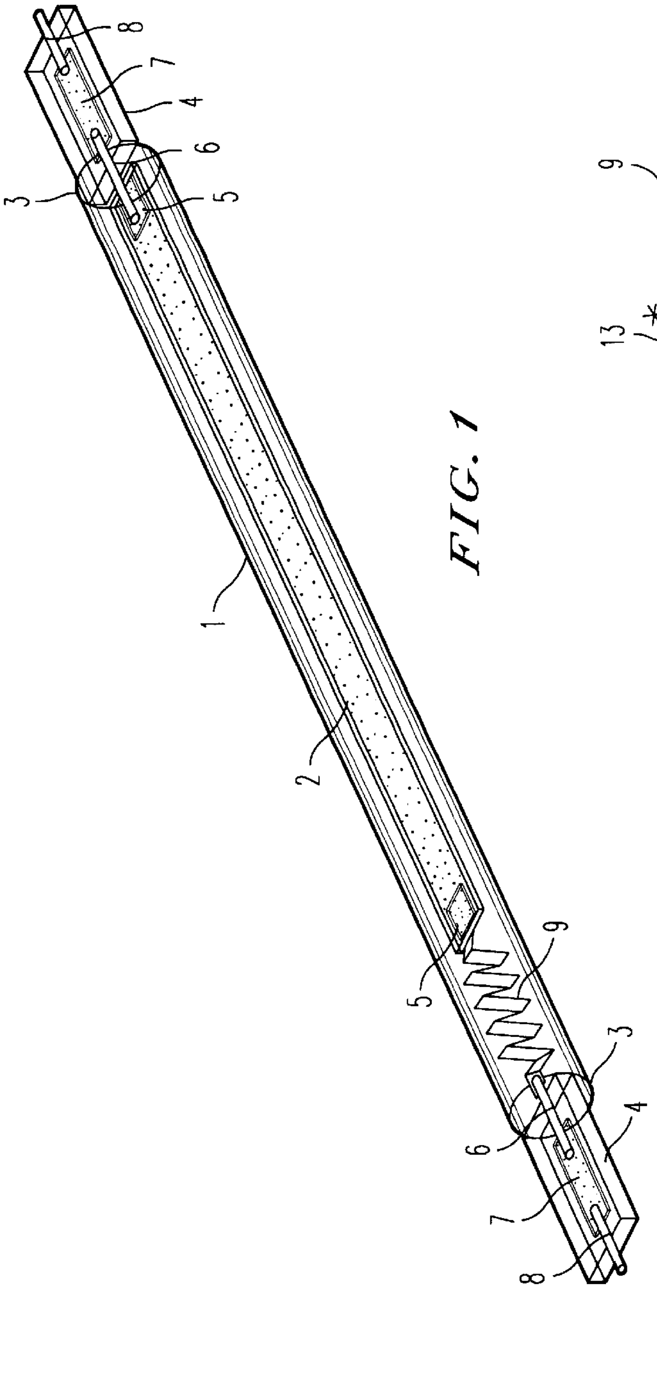
FIG. 1 shows a perspective view of a radiator according to the present invention.

It has been found, especially in the manufacture of radiant devices with relatively small fluorescent-tube diameters, for example with diameters of 9 mm in the inside space, that an elastic element of helically wound wire, such as is now standard in the prior art, cannot be used, since with relatively small envelope-tube diameters (less than 12 mm inside) a helical spring of stranded molybdenum wire, which must have sufficiently large cross section to withstand the high current load, becomes inelastic. If the envelope tube were pinched at its ends, there would even exist the danger, due to excessive tensile force, of tearing of the molybdenum sealing foil, which is usually placed around the radiant ribbon in the region of the penetration thereof. In order to compensate for the length expansion of the radiant ribbon or of the radiant source, therefore, there is provided according to the invention a feature which comprises using, as element for compensation for the length change, a molybdenum sheet which contains at least one folding portion, which is sufficient to compensate for the length changes that occur. It has been found that radiators, especially carbon radiators, can be manufactured with very small fluorescent-tube or envelope-tube diameters using a molybdenum sheet folded in this way, since the molybdenum sheet is capable of withstanding the high current loads despite the small available inside cross section of the radiator, since the molybdenum sheet can be designed in such a way that the entire inside diameter of the envelope tube is utilized.

In order to achieve adequate mechanical stability on the one hand and to withstand high current loads on the other hand, the molybdenum sheet should have a thickness in the range of 0.07 to 0.1 mm, with a preferred width of the molybdenum sheets in the range of 0.5 to 0.7 mm per 1 A of current load.

Furthermore, it has proved expedient, especially with regard to the necessary elasticity, to ensure that the width-to-height ratio of the folded molybdenum sheets is in the range of 1:0.5 to 1:1, and preferably is about 1:0.75.

The radiant device as specified is suitable in particular for inside diameters of the envelope tube that are less than 12 mm.

To increase the elasticity, especially if radiant devices with very long envelope tubes are to be constructed, the folding portion can be provided with a plurality of kink points which, when viewed in the axial direction of the envelope tube, are disposed successively in zig-zag or concertina-like manner. For example, if the length of the radiant source is in the range of 400 to 1000 mm, the number of folds or kink points is preferably at least 10. If lengths of the radiant source in the range of greater than 1000 mm are necessary, the number of folds or kink points should be at least 12.

A folding portion of the type to be used can also be disposed in the region of both connecting ends of the radiant source which are joined to the respective connecting pins led out through the pinch at the end of the envelope tube.

In a particularly preferred embodiment, such a folding portion is formed with at least two kink points perpendicular to the longitudinal axis of the envelope tube in combination with a carbon ribbon as the radiant source.

In order to achieve a simple but nevertheless very durable connection of the folding portion to the connecting pin on the one hand and to the radiant source on the other hand, a resistance-welded joint should preferably be used.

An embodiment of a radiant device according to the invention will now be described hereinafter with reference to the drawings.

The radiant device as shown in FIG. 1 in perspective view comprises an envelope tube 1, along the axis of which there is guided a ribbon-like radiant source 2, in the form of a carbon ribbon in the present example. The inside diameter of this envelope tube 1 is about 10 to 12 mm. Envelope tube 1, which is made from transparent quartz, is sealed at each end 3 with a pinch 4.

At each end of radiator ribbon 2 there is fastened a contact plate 5. The one contact plate 5 at the one end 3 of radiant source 2, or the right end in FIG. 1, is connected to a contact pin 6, which penetrates into pinch 4, in the region of which contact pin 6 merges into a molybdenum foil 7, which in turn is connected at its other end with a pin-like electrical connecting part 8, which passes through pinch 4 to the outside, in order to be able to contact the radiator.

At the opposite end, or in other words the left end in FIG. 1, ribbon-like radiant source 2 is in turn joined via a contact plate 5 to an intermediate part 9. This intermediate part 9, which comprises a plurality of folding portions 15, is also shown in an enlarged diagram in FIG. 2. Each folding portion 15 is provided with a plurality of kink points 10; at each free end there is provided a connecting tab 11. Whereas the right end of intermediate part 9 is fastened at its tab 11 to ribbon-like radiant source 2 in the region of contact plate 5, the other end, meaning the other connecting tab 11, is in turn joined to a contact pin 6, which penetrates into pinch 4 and is joined there to a molybdenum foil 7, which in turn joins radiant source 2 via a connecting pin 8 to the outside.

By virtue of intermediate part 9 with folding portions 15, ribbon-like radiant source 2 can undergo length changes while nevertheless conserving its tension at all times. This intermediate part 9 is capable of withstanding the high current loads, since the molybdenum ribbon forming intermediate part 9 or folding portions 15 can be designed with ribbon width 13 and height 16 of individual folding portions 15 such that the entire cross section of the inside space of envelope tube 1 is utilized.

Figure 2:
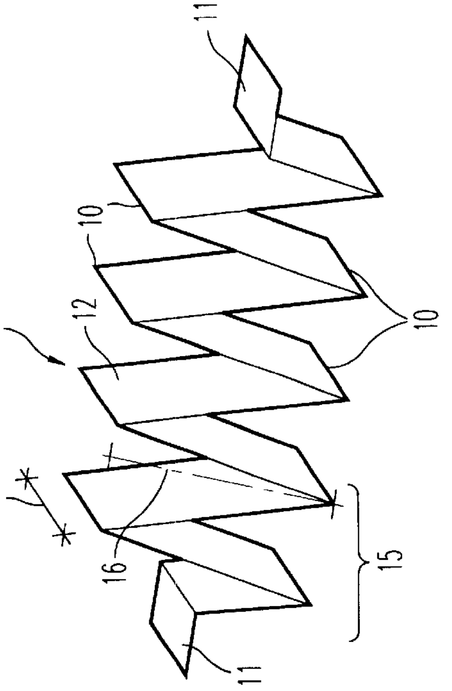
FIG. 2 shows an enlarged diagram of the folding portion of the type used in FIG. 1.

Intermediate part 9, as shown in FIG. 2 and used in the radiant device of FIG. 1, has a total of nine kink points 10, not including kink point 10 in the region of connecting tabs 11. An intermediate part 9 with such dimensions is suitable in particular for radiators having lengths in the range of 1000 to 1500 mm. Width 13 of molybdenum sheet 12 from which intermediate part 9 is formed is such that it corresponds to approximately half the inside diameter of envelope tube 1, on the basis of the dimensioning rule that the width of molybdenum sheets 12 should be 0.5 to 0.7 mm per 1 A of current load. The ratio of width 13 to height 16 (see FIG. 2) of folded molybdenum ribbon 12 is in the range of 1:0.5 to 1:1, a value of about 1:0.75 being regarded as preferred.

The disclosure of German priority patent application 199 17 270.6, filed Apr. 16, 1999, is hereby incorporated by reference.

We claim:

1. A radiant device comprising an envelope tube, which tube contains a long axis, and inside the tube, at least one radiant source oriented in the direction of the long axis of the envelope tube which is sealed at both ends, with a metal, electrical connecting part at each end of the envelope tube, and at least one elastic intermediate part having two ends and which absorbs length changes of the radiant source and which is firmly joined at one end to an electrical connecting part and at the other end to the radiant source, and wherein the intermediate part comprises a molybdenum sheet provided with at least one folding portion having two kink points perpendicular to the long axis.

2. The radiant device according to claim 1, wherein the molybdenum sheet has a thickness in the range of 0.07 to 0.1 mm.

3. The radiant device according to claim 2, wherein the ratio of width to height of the folded molybdenum sheets is 1:0.5 to 1:1.

4. The radiant device according to claim 3, wherein the ratio of width to height of the folded molybdenum sheets is 1:0.75.

5. The radiant device according to claim 3, which is an infrared radiator.

6. The radiant device according to claim 2, which is an infrared radiator.

7. The radiant device according to claim 1, wherein the molybdenum sheet has a width in the range of 0.5 to 0.7 mm.

8. The radiant device according to claim 7, wherein the ratio of width to height of the folded molybdenum sheets is 1:0.5 to 1:1.

9. The radiant device according to claim 8, wherein the ratio of width to height of the folded molybdenum sheets is 1:0.75.

10. The radiant device according to claim 7, which is an infrared radiator.

11. The radiant device according to claim 1, wherein the ratio of width to height of the folded molybdenum sheets is 1:0.5 to 1:1.

12. The radiant device according to claim 11, wherein the ratio of width to height of the folded molybdenum sheets is 1:0.75.

13. The radiant device according to claim 11, which is an infrared radiator.

14. The radiant device according to claim 1, wherein the inside diameter of the envelope tube is less than 12 mm.

15. The radiant device according to claim 1, wherein the folding portion is provided with a plurality of kink points which, viewed in axial direction of the envelope tube, are disposed successively in zig-zag or concertina-like manner.

16. The radiant device according to claim 15, wherein, for a length of the radiant source in the range of 400 to 1000 mm, the number of kink points is at least 10.

17. The radiant device according to claim 15, wherein, for a length of the radiant source in the range of greater than 1000 mm, the number of kink points is at least 12.

18. The radiant device according to claim 1, wherein the radiant source comprises a carbon ribbon.

19. The radiant device according to claim 1, wherein the intermediate part is joined by resistance welding to the connecting part and to a ribbon-contacting part on the radiant source.

20. The radiant device according to claim 1, which is an infrared radiator.

* * * * *